United States Patent
Das et al.

(10) Patent No.: US 6,872,829 B2
(45) Date of Patent: Mar. 29, 2005

(54) PROCESS FOR THE DIRECT PREPARATION OF 5-ALKOXY AND 5-ACYLOXY ANALOGUES OF CAMPTOTHECINS OR MAPPICENE KETONES

(75) Inventors: Biswanath Das, Andhra Pradesh (IN); Purushotham Madhusuda, Andhra Pradesh (IN); Venkata Naga Satya Srinivas Kalavagunta, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 77 days.

(21) Appl. No.: 10/334,673

(22) Filed: Dec. 30, 2002

(65) Prior Publication Data

US 2004/0127711 A1 Jul. 1, 2004

(51) Int. Cl.[7] .................... C07D 471/00; G01N 33/00
(52) U.S. Cl. ................ 546/48; 436/128; 436/174; 436/178
(58) Field of Search ............... 546/48; 436/128, 436/110, 111, 174, 177, 178; 544/125, 361

(56) References Cited

U.S. PATENT DOCUMENTS

| | | | |
|---|---|---|---|
| 3,894,029 A | | 7/1975 | Winterfeldt et al. |
| 4,399,282 A | * | 8/1983 | Miyasaka et al. ............. 546/48 |
| 4,473,692 A | * | 9/1984 | Miyasaka et al. ............. 546/48 |
| 4,894,456 A | * | 1/1990 | Wall et al. .................... 546/41 |
| 4,981,968 A | * | 1/1991 | Wall et al. ................... 544/361 |
| 5,004,758 A | * | 4/1991 | Boehm et al. ............... 514/283 |
| 5,061,800 A | * | 10/1991 | Yaegashi et al. ............. 546/48 |
| 5,734,056 A | | 3/1998 | Burk et al. |

FOREIGN PATENT DOCUMENTS

| | | |
|---|---|---|
| EP | 1138682 A1 | 10/2001 |
| JP | 59-5188 | * 1/1984 |

OTHER PUBLICATIONS

Subrahmanyam, et al., "Novel C–Ring Analogues of 20(s)–captothecin. Part 3: Synthesis and Their In Vitro Cytotoxicity of A–, B– and C–ring Analogues", Bioorganic & Medicinal Chemistry Letters, Oxford, GB, vol. 10, No. 4, Feb. 2000, pp. 369–371.

* cited by examiner

Primary Examiner—Maureen M. Wallenhorst
(74) Attorney, Agent, or Firm—Darby & Darby

(57) ABSTRACT

A convenient and efficient process for direct preparation of 5-alkoxy and 5-acyloxy analogues of camptothecins (anticancer compounds) and mappicine ketones (antiviral compounds) has been invented by treatment of the parent compounds with alcohols and acids respectively in the presence of ceric ammonium nitrate (CAN) at room temperature. The process is simple, economic and completed within a short period of time.

11 Claims, No Drawings

PROCESS FOR THE DIRECT PREPARATION OF 5-ALKOXY AND 5-ACYLOXY ANALOGUES OF CAMPTOTHECINS OR MAPPICENE KETONES

FIELD OF THE INVENTION

The present invention relates to a method for direct preparation of 5-alkoxy and 5-acyloxy analogues of camptothecins or mappicine ketones.

BACKGROUND OF THE INVENTION

Camptothecin (I) is a naturally occurring pyrrolo (3,4-b)-quinoline alkaloid having remarkable antitumour and anti-leukemic activities (Wall et. al., *J. Am. Chem. Soc.* 88, 3888, 1966). It acts as an inhibitor of DNA topoisomerase I (Hsiang et al., *J. Biol. Chem.*, 260, 14873, 1985). Two natural analogues of the compound, 9-methoxy camptothecin (II) (Govindachari and Viswanathan, *Phytochemistry*, 11, 3529, 1972; Wu et al., *Phytochemistry*, 39, 383, 1995) and 20-O-acetyl camptothecin (III) (Wu et al., *Phytochemistry*, 39, 383, 1995; Das et al., *Indian J. Chem*, 36B, 207, 1997) also possess significant cytotoxic property. The decarboxylated E-ring analogues of camptothecin (I) and 9-methoxycamptothecin (II), known as mappicine ketone (nothapodytine B) (IV) and 9-methoxymappicine ketone (nothapodytine A) (V) respectively are also naturally occurring alkaloids (Wu et al., *Phytochemistry*, 42, 907, 1996; Pendrak et al., *J. Org. Chem*, 59, 2623, 1994). Mappicine ketone (IV) has recently been identified as an antiviral lead (Pendrak et al., *J. Org. Chem.*, 59, 2623, 1994; *J. Org. Chem.* 60, 2912, 1995).

As a drug camptothecin (I) itself has several problems including its high toxicity and low water solubility. So several analogues of the compound have been prepared to evaluate their clinical efficacies. Recently different 5-substituted alkoxycamptothecins have been found to exhibit potent anticancer activity (Subrahmanyam et.al., *Bioorg. Med, Chem. Lett.*, 10, 369, 2000). The methods of preparation of 5-alkoxy camptothecins are limited. They were prepared earlier from 5-hydroxycamptothecin which was obtained by treatment of camptothecin with $I_2$ and $K_2CO_3$ in DMF. 5-Hydroxycamptothecin was subsequently converted into 5-alkoxycamptothecins by reacting with alcohols in the presence of $BF_3.OEt_2$ (Swada et al., *Chem. Pharm Bull.*, 39,2574,1991). This is a two-step process and so the overall yields of 5-alkoxycamptothecins will be diminished. The experimental procedures are also tidious. In the other approach camptothecin was heated with $FeCl_3$-$H_2SO_4$ in EtOH for 20 hr to obtain a mixture of 5-ethoxy and 5-hydroxycamptothecins. The mixture was again heated with aqueous HCl for 20 hr to obtain 5-hydroxycamptothecin exclusively. This 5-hydroxycamptothecin was then treated with different alcohols in the presence of p-toluenesulfonic acid to prepare 5-alkoxycamptothecins (Subrahmanyam et al., *Biorg. Med. Chem. Lett.*, 10, 369, 2000). This method involves several steps and the time required is high.

OBJECT OF THE INVENTION

The main object of the invention is to provide a convenient and facile process for the direct preparation of 5-alkoxy and 5-acyloxy analogues of camptothecins and mappicene ketones.

It is another object of the invention to provide a process for direct preparation of 5-alkoxy and 5-acyloxy analogues of camptothecins and mappicene ketones in high yield.

It is yet another object of the invention to provide a process for direct preparation of 5-alkoxy and 5-acyloxy analogues of camptothecins and mappicene ketones which is simple and non-hazardous.

SUMMARY OF THE INVENTION

Accordingly the present invention provides a process for the direct preparation of 5-alkoxy and 5-acyloxy analogues of camptothecins or mappicene ketones comprising reacting camptothecin or mappicene ketone dissolved in an organic solvent or an acid with ceric ammonium nitrate in an organic solvent at a temperature in the range of 20 to 30° C. for a period in the range of 2 to 10 hours, concentrating the reaction mixture and adding water to the concentrate followed by extraction with ethyl acetate to obtain the desired product.

In one embodiment of the invention, the camptothecin is selected from the group consisting of camptothecin (I), 9-methyl camptothecin (II) and 20-O-acetyl camptothecin (III).

In yet another embodiment of the invention, the organic solvent used for the camptothecin solution is selected from the group consisting of dichloromethane chloroform, tetrahydrofuran and any mixture thereof.

In a further embodiment of the invention, the organic acid used for the camptothecin solution is selected from acetic acid, propanoic acid and benzoic acid.

In yet another embodiment of the invention, the analogues obtained comprise the group of 5-methoxy camptothecin, 5-isopropoxy camptothecin, 5-ethoxy-9-methoxy camptothecin, 5-methoxy mappicene ketone, 5-ethoxy-9-methoxy mappicene ketone, 5-acetoxy camptothecin, 5-acetoxy-9-methoxy camptothecin, 5-propionoxy-20-O-acetylcamptothecin, 5-benzoyloxymappicene ketone and 5-acetoxy-9-methoxymappicene ketone.

DETAILED DESCRIPTION OF THE INVENTION

The present investigation has led to the development of a convenient and facile method for direct preparation of 5-alkoxy and 5-acyloxy analogues of camptothecins and mappicine ketones. Camptothecin (I), 9-methoxycamptothecin (II) and 20-O-acetylcamptothecin (III) as well as mappicine ketone (IV) and 9-methoxymappicine ketone (V) were isolated from the stems of Indian *Nothapodytes foetida*. Camptothecins and mappicine ketones on treatment with alcohols in the presence of ceric ammonium nitrate (CAN) at room temperature for 2 hr afforded 5-alkoxy compounds in very high yields (72–86%). Both primary and secondary alcohols were used. 5-Alkoxycamptothecins were found (from their $^1$H NMR spectra) to be mixtures (1:1) of both the diastereoisomers with 20-(S), 5-(S) and 20-(S), 5-(R) configurations.

The mixtures were not further separated since anticancer activity was reported earlier on the mixtures (Subrahmanyam et. al., *Bioorg. Med. Chem. Lett*, 10, 369, 2000). However, for mappicine ketones each 5-alkoxy analogue was obtained as a racemic compound. During the present study several 5-acyloxy analogues of camptothecins and mappicine ketones have also been prepared.

Previously some 5-acyloxycamptothecins were prepared in two steps from camptothecins via their 5-hydroxy derivatives (Swada et al., *Chem. Pharm Bull.*, 39, 2574, 1991). It is observed that when camptothecins were treated with acids (both aliphatic and aromatic) in the presence of CAN at room temperature for 8 hr 5-acyloxycamptothecins were obtained (as 1:1 diastereoisomeric mixtures). Hydroxy group at C-20 remained unaffected. Mappicine ketones also underwent similar conversion within 6 hr into 5-acyloxy analogues when treated with acids in the presence of CAN. The yields of the 5-acyloxycamptothecins and mappicine ketones were very high (71–82%).

The present procedure for the preparation of useful 5-substituted alkoxy and acyloxy derivatives of camptothecins and mappicine ketones is very simple and efficient. The conversion is completed within a short period of time. The reaction proceeds at room temperature and not involves any hazardous and costly reagent. The yields of the products are very high. Thus the process of the invention is useful and practical for the preparation of 5-alkoxy and 5-acyloxy analogues of camptothecins and mappicine ketones. All the analogues of mappicine ketones are new compounds.

The time taken for obtaining the products is about 2 hours for 5-alkoxy compounds and 6–8 hours for 5-acyloxy compounds. Another significant advantage of the invention is that the yields of the products are high (72–86% for 5-alkoxy compounds and 71–82% for 5-acyloxy compounds). In addition, the solvents used for extraction can be recovered rendering the process more economic. A process as claimed in Claims 1–6 wherein a library of 5-alkoxy and 5-acyloxycamptothecins and mappicine ketones can easily be generated to discover promising anticancer and anti-viral agents.

The prepared 5-alkoxy and 5-acyloxy analogues of camptothecins and mappicine ketones are useful for preparation of different other analogues which in turn are useful for discovery of novel and potent anticancer and antiviral drugs.

The reaction mechanism is given below:

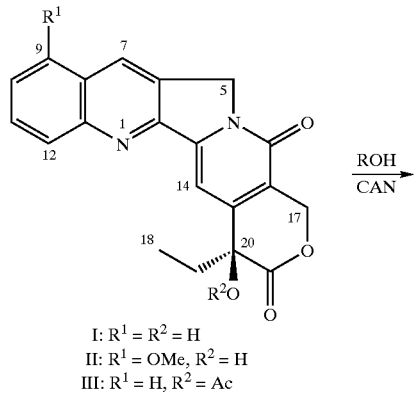

I: $R^1 = R^2 = H$
II: $R^1 = OMe, R^2 = H$
III: $R^1 = H, R^2 = Ac$

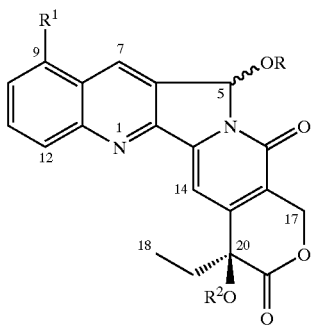

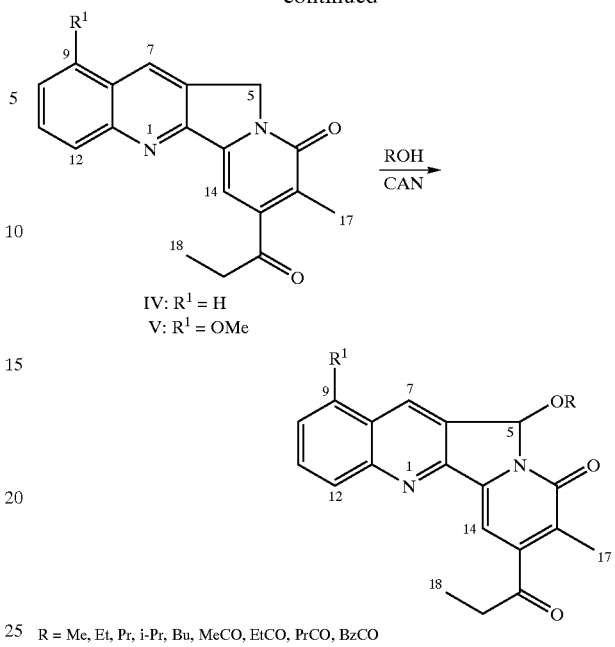

IV: $R^1 = H$
V: $R^1 = OMe$

R = Me, Et, Pr, i-Pr, Bu, MeCO, EtCO, PrCO, BzCO

The present invention is now described with reference to the following examples which are illustrative and should not be construed as limiting the scope of the invention in any manner.

EXAMPLE: 1

To a well stirred solution of CAN (100 mg) in MeOH (10 ml) camptothecin (I) (100 mg) in THF-$CH_2Cl_2$ (1:1) (20 ml) was added. The mixture was stirred at room temperature for 2 hr. After concentration, water (20 ml) was added. The mixture was extracted with EtOAc (3×10 ml) and concentrated. Impurities were removed by column chromatography over silica gel to obtain 5-methoxycamptothecin (88 mg).

EXAMPLE: 2

Camptothecin (I) (100 mg) in a mixture of THF-$CH_2Cl_2$ (1:1) (20 ml) was added to a solution of CAN (100 mg) in isopropanol (10 ml) and the mixture was stirred at room temperature for 2 hr. The mixture was concentrated and water (20 ml) was added. This was extracted with EtOAc (3×10 ml) and concentrated. The residue was subjected to column chromatography over silica gel for removal of the impurities to afford 5-isopropoxycamptothecin (84 mg).

EXAMPLE: 3

9-Methoxycamptothecin (II) (100 mg) in $CH_2Cl_2$ (20 ml) was added to a well stirred solution of CAN (100 mg) in EtOH (10 ml). The stirring was continued at room temperature for 2 hr. The mixture was concentrated and water (20 ml) was added. This was extracted with EtOAc (3×10 ml). The concentrated extract on column chromatography over silica gel produced 5-ethoxy-9-methoxycamptothecin (81 mg).

EXAMPLE: 4

A solution of CAN (100 mg) in MeOH (10 ml) was stirred at room temperature. A solution of 20-O-acetylcamptothecin (III) (100 mg) in CHCl$_3$ (20 ml) was added. The mixture was stirred for 2 hr. This was concentrated and water (20 ml) was added. The mixture was extracted with EtOAc (3×10 ml), concentrated and subjected to column chromatography over silica gel to yield 5-methoxy-20-O-acetyl camptothecin (82 mg).

EXAMPLE: 5

To a well-stirred solution of CAN (100 mg) in MeOH (10 ml) mappicine ketone (100 mg) in CHCl$_3$ (20 ml) was added. The mixture was stirred at room temperature for 2 hr. The mixture was concentrated and water (20 ml) was added to this. This was extracted with EtOAc (3×10 ml). The concentrated extract was purified by column chromatography over silica gel to yield 5-methoxy mappicine ketone (95 mg).

EXAMPLE: 6

9-Methoxymappicine ketone (V) (100 mg) in CHCl$_3$ (20 ml) was added to a solution of CAN (100 mg) in ethanol (10 ml). The mixture was stirred at room temperature for 2 hr. This was concentrated and to the concentrated mass water (20 ml) was added. This was extracted with EtOAc (3×10 ml), concentrated and purified by column chromatography over silica gel to afford 5-ethoxy-9-methoxymappicine ketone (92 mg).

EXAMPLE: 7

Camptothecin (I) (100 mg) was taken in AcOH (10 ml) and CAN (100 mg) was added. The mixture was stirred at room temperature for 8 hr. Water (20 ml) was added. The mixture was extracted with EtOAc (3×10 ml). The extract was concentrated and the impurities were removed by column chromatography over silica gel to yield 5-acetoxycamptothecin (93 mg).

EXAMPLE: 8

CAN (100 mg) was added to a mixture of camptothecin (100 mg) and propionic acid (10 ml) and this was stirred at room temperature for 8 hr. Water (20 ml) was added and the mixture was extracted with EtOAc (3×10 ml). The solvent was removed from the extract and the residue was subjected to column chromatography over silica gel to obtain 5-propionoxycamptothecin (90 mg).

EXAMPLE: 9

CAN (100 mg) was added to a well stirred solution of 9-methoxycamptothecin (100 mg) in acetic acid (10 ml) and the stirring was continued for 8 hr at room temperature. Water (20 ml) was added to the mixture and extracted with EtOAc (3×10 ml). The extract was concentrated and the impurities were removed by column chromatography over silica gel to yield 5-acetoxy-9-methoxycamptothecin (89 mg).

EXAMPLE: 10

To a solution of 20-O-acetyl camptothecin (100 mg) in propionic acid (10 ml) CAN (100 mg) was added and the mixture was stirred at room temperature for 8 hr. Water (20 ml) was added and the mixture was extracted with EtOAc (3×10 ml). The concentrated extract on chromatography over silica gel afforded 5-propionoxy-20-O-acetylcamptothecin (85 mg)

EXAMPLE: 11

To a solution of mappicine ketone (100 mg) in CHCl$_3$ (10 ml) benzoic acid (100 mg) and CAN (100 mg) were added. The mixture was stirrred for 6 hr at room temperature and water (20 ml) was added. This was extracted with EtOAc (3×10 ml) and the extract was concentrated. The residue was purified by column chromatography over silica gel to produce 5-benzoyloxymappicine ketone (99 mg).

EXAMPLE: 12

CAN (100 mg) was added to 9-methoxymappicine ketone (100 mg) dissolved in AcOH (10 ml). The mixture was stirred at room temperature for 6 hr. Water (20 ml) was added and the mixture was extracted with EtOAc (3×10 ml). The extract on purification by column chromatography over silica gel yielded 5-acetoxy-9-methoxymappicne ketone (89 mg).

The Main Advantages of the Present Invention Are:
1. This is a direct method for preparation of 5-alkoxy and 5-acyloxy analogues of camptothecins and mappicine ketones.
2. The process is very simple.
3. The preparation of 5-alkoxy/acyloxy camptothecins and mappicine ketones is completed within a short period of time.
4. The reactions proceed at room temperature with an easily available and non-hazardous reagent (CAN).
5. The yields of the products are very high.

We claim:

1. A process for the direct preparation of 5-alkoxy and 5-acyloxy analogues of camptothecins or mappicene ketones comprising reacting camptothecin or mappicene ketone dissolved in an organic solvent or an acid, with ceric ammonium nitrate in an organic solvent to obtain a reaction mixture, concentrating the reaction mixture and adding water to the concentrate followed by extraction with ethyl acetate to obtain 5-alkoxy and 5-acyloxy analogues of camptothecins or mappicene ketones.

2. A process as claimed in claim 1 wherein the camptothecin is selected from the group consisting of camptothecin (I), 9-methyl camptothecin (II), and 20-O-acetyl camptothecin (III).

3. A process as claimed in claim 1 wherein the mappicene ketone used comprises 9-methoxymappicene ketone.

4. A process as claimed in claim 1 wherein the organic solvent in which the camptothecin is dissolved is selected from the group consisting of dichloromethane, chloroform, tetrahydrofuran and any mixture thereof.

5. A process as claimed in claim 1 wherein the acid in which the camptothecin is dissolved is an organic acid selected from the group consisting of acetic acid, propanoic acid and benzoic acid.

6. A process as claimed in claim 1 wherein the ceric ammonium nitrate is used in the form of a solution in a solvent selected from the group consisting of methanol, propanol, isopropanol and ethanol.

7. A process as claimed in claim 1 wherein the reaction is carried out at a temperature in the range of 20 to 30° C. for a period in the range of 2 to 10 hours.

8. A process as claimed in claim 1 wherein the analogues obtained are selected from the group consisting of 5-methoxy camptothecin, 5-isopropoxy camptothecin, 5-ethoxy-9-methoxy camptothecin, 5-methoxy mappicene ketone, 5-ethoxy-9-methoxy mappicene ketone, 5-acetoxy camptothecin, 5-acetoxy-9-methoxy camptothecin, 5-propionoxy-20-O-acetylcamptothecin, 5-benzoyloxy-mappicene ketone and 5-acetoxy-9-methoxymappicene ketone.

9. A process as claimed in claim 1 wherein the 5-alkoxy and 5-acyloxy analogues of camptothecin or mappicene ketone are obtained in a yield 72–86% for 5-alkoxy analogues and 71–82% for 5-acyloxy analogues.

10. A process as claimed in claim 1 wherein the ethyl acetate used is recovered.

11. A process as claimed in claim 1 wherein conversion of camptothecin or mappicene ketone to a corresponding 5-alkoxy and 5-acyloxy analogue thereof occurs in a single step.

* * * * *

UNITED STATES PATENT AND TRADEMARK OFFICE
CERTIFICATE OF CORRECTION

PATENT NO. : 6,872,829 B2
DATED : March 29, 2005
INVENTOR(S) : Biswanath Das et al.

It is certified that error appears in the above-identified patent and that said Letters Patent is hereby corrected as shown below:

<u>Title page,</u>
Item [75], Inventors, delete "Purushotham Madhusuda, Andhra Pradesh (IN)" and substitute with -- Madhusudan Purushotham, Andhra Pradesh (IN) --.

Signed and Sealed this

Seventh Day of June, 2005

JON W. DUDAS
*Director of the United States Patent and Trademark Office*